US006283982B1

(12) United States Patent
Levaughn et al.

(10) Patent No.: US 6,283,982 B1
(45) Date of Patent: Sep. 4, 2001

(54) LANCING DEVICE AND METHOD OF SAMPLE COLLECTION

(75) Inventors: Richard W. Levaughn, McDonough; Stephen J. Flynn, Peachtree City; Gwenn E. Kennedy, Ellenwood; Michael V. Lipoma, Villa Rica, all of GA (US)

(73) Assignee: Facet Technologies, Inc., Marietta, GA (US)

( * ) Notice: Subject to any disclaimer, the term of this patent is extended or adjusted under 35 U.S.C. 154(b) by 0 days.

(21) Appl. No.: 09/420,649

(22) Filed: Oct. 19, 1999

(51) Int. Cl.[7] ................................................ A61B 17/32

(52) U.S. Cl. ........................................ 606/172; 606/182

(58) Field of Search .................................. 606/182, 172, 606/183; 604/136, 137, 156, 157; 600/583

(56) References Cited

U.S. PATENT DOCUMENTS

| Re. 32,922 | * | 5/1989 | Levin et al. . | |
|---|---|---|---|---|
| D. 369,864 | | 5/1996 | Petersen . | |
| D. 379,516 | | 5/1997 | Rutter . | |
| 1,135,465 | | 4/1915 | Pollock . | |
| 4,360,016 | | 11/1982 | Sarrine ........................... | 128/763 |
| 4,388,925 | | 6/1983 | Burns . | |
| 4,416,279 | | 11/1983 | Lindner et al. .................. | 128/314 |
| 4,426,105 | | 1/1984 | Plaquin et al. . | |
| 4,442,836 | * | 4/1984 | Meinecke et al. ............... | 604/137 |
| 4,503,856 | | 3/1985 | Cornell et al. . | |
| 4,517,978 | | 5/1985 | Levin et al. .................... | 128/314 |
| 4,527,561 | | 7/1985 | Burns . | |
| 4,535,769 | | 8/1985 | Burns . | |
| 4,553,541 | | 11/1985 | Burns . | |
| 4,653,313 | | 3/1987 | Sabins et al. .................. | 73/61.4 |
| 4,785,858 | | 11/1988 | Valentini et al. . | |
| 4,834,667 | | 5/1989 | Fowler et al. . | |
| 4,858,607 | | 8/1989 | Jordan et al. . | |
| 4,895,147 | * | 1/1990 | Bodicky et al. ................ | 606/182 |
| 4,920,977 | * | 5/1990 | Haynes ......................... | 128/770 |
| 4,924,879 | | 5/1990 | O'Brien . | |
| 4,976,724 | | 12/1990 | Nieto et al. . | |
| 5,279,294 | | 1/1994 | Andreson et al. . | |

(List continued on next page.)

FOREIGN PATENT DOCUMENTS

| 523078 | 3/1956 | (CA) . |
| WO 97/42886 | 11/1997 | (WO) . |

OTHER PUBLICATIONS

Roche, "Soft Touch II" lancing device.
Roche, "Autoclix" lancing device.
Bayer, "Microlet" lancing device.
Bayer, "Vaculance" lancing device.
Lifescan/Johnson & Johnson, "Penlet Plus" lancing device.
Palco, "Auto-Lancet" lancing device.
Bechton-Dickinson, "Autolance" lancing device.
Bayer, "Ames Glucolet" lancing device.
Lifescan, "Penlet II" lancing device.
Lifescan, "Penlet" lancing device.
Bleeding From Standardized Skin Punctures: Automated Technic for Recording Time, Intensity, and Pattern of Bleeding; Sutor et al.; May 1971.

*Primary Examiner*—Michael H. Thaler
(74) *Attorney, Agent, or Firm*—Gardner Groff Mehrman & Josephic, P.C.

(57) ABSTRACT

A lancing device and method for self-collecting a sample of body fluid by penetrating a body tissue at a sampling site. The invention includes a housing geometry configured for ease of use at different sampling sites on the body, even by persons having reduced dexterity and/or poor vision. Depth of penetration is selectively controlled by adjusting the stroke range of a spring-driven lancet carrier. A pressure applicator is included for stimulating flow of the body fluid. A transparent portion permits observation of the sampling site.

10 Claims, 6 Drawing Sheets

U.S. PATENT DOCUMENTS

| | | | |
|---|---|---|---|
| 5,304,193 | 4/1994 | Zhadanov . | |
| 5,318,584 | 6/1994 | Lange et al. | 606/182 |
| 5,324,303 | 6/1994 | Strong et al. . | |
| 5,368,047 | 11/1994 | Suzuki et al. | 128/765 |
| 5,454,828 | 10/1995 | Schraga . | |
| 5,464,418 * | 11/1995 | Schraga | 606/182 |
| 5,554,166 | 9/1996 | Lange et al. | 606/182 |
| 5,569,287 | 10/1996 | Tezuka et al. . | |
| 5,613,978 | 3/1997 | Harding . | |
| 5,628,764 * | 5/1997 | Schraga | 606/182 |
| 5,628,765 | 5/1997 | Morita . | |
| 5,666,966 | 9/1997 | Horie et al. | 128/760 |
| 5,730,753 | 3/1998 | Morita . | |
| 5,857,983 | 1/1999 | Douglas et al. | 600/538 |
| 5,868,772 | 2/1999 | LeVaughn et al. | 606/181 |
| 5,871,494 | 2/1999 | Simons et al. | 606/181 |
| 5,872,713 | 2/1999 | Douglas et al. | 364/413.09 |
| 5,873,887 | 2/1999 | King et al. | 606/182 |
| 5,876,957 | 3/1999 | Douglas et al. | 435/28 |
| 5,879,311 | 3/1999 | Duchon et al. | 600/583 |
| 5,885,211 | 3/1999 | Eppstein et al. | 600/309 |
| 5,885,790 | 3/1999 | Douglas et al. | 435/28 |
| 5,916,230 | 6/1999 | Brenneman et al. . | |
| 5,951,493 | 9/1999 | Douglas et al. . | |
| 5,951,582 | 9/1999 | Thorne et al. . | |
| 5,954,738 | 9/1999 | LeVaughn et al. | 606/181 |
| 5,984,940 | 11/1999 | Davis et al. . | |
| 6,022,366 | 2/2000 | Schraga . | |
| 6,027,459 | 2/2000 | Shain et al. . | |
| 6,045,567 | 4/2000 | Taylor et al. . | |
| 6,056,701 | 5/2000 | Duchon et al. . | |
| 6,086,545 | 7/2000 | Roe et al. . | |
| 6,099,484 | 8/2000 | Douglas et al. . | |
| 6,156,051 | 12/2000 | Schraga . | |

* cited by examiner

LANCING DEVICE AND METHOD OF SAMPLE COLLECTION

FIELD OF THE INVENTION

The present invention relates generally to devices and methods for use in medical sampling and testing, and more particularly to a lancing device and a method for penetrating body tissue to obtain a sample of body fluid.

BACKGROUND OF THE INVENTION

Samples of blood, interstitial fluid, or other body fluids are commonly required for various medical purposes. For example, many diabetics must periodically monitor their blood glucose level to determine when an insulin injection is needed. Self-testing systems are available to enable a person to obtain a sample of his or her own blood, typically by penetrating the skin, and to subject the harvested blood sample to analysis of the blood glucose level. Often, a lancing device is used to penetrate the skin to obtain the required sample of blood. For example, U.S. Pat. Nos. 5,954,738; 5,879,311; 5,857,983; and 5,318,584 disclose particular forms of body fluid sampling devices.

In order to encourage compliance in regular usage, it is highly desirable that the use of a lancing device be as painless as possible to a subject obtaining a blood sample. Because the fingertips are rich in capillaries, a number of lancing devices have been designed for sample collection from this region. Nerve density is high in the fingertips, however, and significant pain often results from fingertip sampling. Moreover, repeated sampling can adversely result in callous formation on the fingertips. Accordingly, testing procedures have been developed allowing sampling at other sites on the body, such as the earlobe or forearm. By appropriate selection of the sampling site, the lancet geometry and the depth of penetration, the required sample size is obtained. According to present and developing sampling methods, sample sizes of about 8–10 microliters ($\mu$L), and in some instances about 2–3 microliters ($\mu$L), and possibly as little as about 400 nanoliters (nL) are sufficient for blood glucose analysis. It is anticipated that continuing developments in the field will progressively reduce the required sample size. In order to minimize pain and speed healing, it is desirable to minimize the size of the opening in the skin that is required to obtain a sample of the requisite size. To further reduce pain, it is also desirable that the lancing operation incorporate a quick penetration and retraction stroke, wherein the piercing instrument penetrates the skin and is quickly retracted along a substantially linear path.

It has also been found advantageous to provide a lancing device that is configured for ease of manipulation and use at different sampling sites. This is of particular importance with lancing devices intended for use by diabetics, as many diabetics suffer from poor eyesight and neuropathy, often resulting in reduced manual dexterity. Many previously known lancing devices have been found particularly difficult for such users to manipulate in carrying out certain sampling methods. For example, pen-shaped lancing devices are often too narrow for some users to grasp easily, and their cylindrical shape may render them difficult for some users to hold without unintentional twisting of the barrel of the device. Also, because such devices are typically relatively long compared to their width (or diameter) it is difficult for some users to apply sufficient pressure to maintain the device in a stable manner against the user's forearm during sampling. Other lancing devices incorporate non-symmetric or non-rectangular housings and/or housings with gripping surfaces or sample site contacting surfaces that are offset at oblique angles from the stroke axis of their lancets. Such devices are generally adapted for fingertip sampling, but are not well-suited for sampling at a site on the forearm. In particular, due to their angular offset, many users find it difficult to press these lancing devices against the forearm while maintaining the device in an orientation for lancing perpendicularly to the skin.

A number of previously known lancing devices enable penetration of the skin to a single, predetermined depth. Because of differences between individual users, such devices may generate a sample size larger or smaller than necessary. Accordingly it is desirable to provide a lancing device that enables easy adjustment of the depth of penetration, and that provides a reliable and accurate depth stop for providing a desired depth of penetration.

For purposes of commercial appeal to consumers, it has been found desirable to provide a lancing device that is compatible with standard, commercially available, disposable lancets. It is preferable that a standard lancet be readily mountable to a lancing device prior to use, and that the lancet also be readily and safely removable from the lancing device for deposit in a sharps container or other disposal canister. Particular forms of previously known lancing devices have incorporated an eject feature that permits a lancet to be "launched" from the device, potentially resulting in injury. Other known devices require the user to grasp the used lancet for removal, thereby presenting a risk of needle sticks. Accordingly, it would be preferable to provide a lancing device enabling safer and more controlled release of a lancet.

Certain previously known sampling devices provide for the application of pressure to tissue surrounding an incision to stimulate the formation of a drop of sampled fluid. The configuration of previously known stimulator members has been found to provide less than optimal sampling rates, to result in undesirable levels of user discomfort, and to result in bruising or marking of the skin with pressure indentations. In addition, it is often difficult to monitor the sample size produced during use of such previously known devices. Accordingly, it would be preferable to provide a lancing device providing improved stimulation of sample generation and easier monitoring of sample size.

Thus it can be seen that a need exists for an improved lancing device and methods for penetrating tissue to facilitate collection of a sample of a body fluid. It is to the provision of improved lancing devices and methods meeting these and other needs that the present invention is primarily directed.

SUMMARY OF THE INVENTION

The present invention comprises improved lancing devices and methods for penetrating tissue to facilitate collection of a sample of a body fluid. In a preferred aspect, the present invention comprises a lancing device for use with a lancet to penetrate tissue and facilitate collection of a sample of a body fluid. The lancing device preferably includes a housing; a lancet carrier translationally mounted to the housing for carrying a lancet along a stroke traversing an extended position wherein a tissue penetrating portion of the lancet extends a distance outwardly of the housing, the lancet carrier comprising a limit member; and a thumbwheel rotationally mounted to the housing, and comprising an eccentric contact surface forming a selectively movable stop for contacting the limit member to limit the stroke of the lancet carrier in the direction of the extended position.

Accordingly, depth of penetration is easily and accurately adjusted to suit the needs of the individual user, and to produce the required sample size with minimal pain to the user and promote quick healing. Additionally, by minimizing the size of the wound necessary to generate a desired sample size, the wound closes quickly after sampling to reduce the incidence of residual bleeding that may stain the user's clothing.

The lancing device of the present invention preferably engages a standard lancet, and also provides safe and controlled release of the lancet for disposal. In a preferred aspect, the lancing device of the present invention includes a housing, and a lancet carrier mounted to the housing for releasably engaging a lancet. The lancet carrier preferably comprises a first gripping jaw; a second gripping jaw positioned in opposition to the first gripping jaw to define a lancet-receiving channel between the first and second gripping jaws, the first and second gripping jaws being movable between a closed position for gripping a lancet and an open position for receiving and releasing a lancet; biasing means for biasing the first and second gripping jaws toward the closed position; and a first release arm connected to the first gripping jaw and a second release arm connected to the second gripping jaw, whereby application of force to the first and second release arms moves the first and second gripping jaws toward the open position.

In another preferred aspect, the present invention comprises a lancing device for use with a lancet to penetrate tissue and facilitate collection of a sample of a body fluid. The lancing device preferably includes a housing having a forward end and a transparent portion adjacent the forward end. The lancing device preferably further includes a lancet carrier mounted to the housing for carrying a lancet between a retracted position within the housing and an extended position wherein a tissue penetrating portion of the lancet extends a distance beyond the forward end of the housing. The lancing device preferably further includes a pressure applicator adjacent the forward end of the housing.

In another preferred aspect, the present invention comprises a lancing device for use with a lancet to penetrate tissue and facilitate collection of a sample of a body fluid. The lancing device preferably includes a housing having an overall length, an overall width, and an overall thickness, the overall length being no more than about four times the overall width, and the overall width being at least about one and one-half times the overall thickness, wherein the housing is generally symmetric about perpendicular first and second planes of symmetry, and wherein a trigger button is arranged approximately midway along a front face of the housing.

In another preferred aspect, the present invention is a method of collecting a sample of a body fluid. The method preferably comprises forming an opening in a body tissue at a sample site using a lancing device; applying compressive pressure to the sample site with a portion of the lancing device; and observing the sample site through a transparent portion of the lancing device.

These and other objects, advantages, and features of the present invention will become apparent upon reading the following specification in conjunction with the accompanying drawing figures. The advantages of the invention will be realized and attained by means of the elements and combinations particularly pointed out in the appended claims. It is to be understood that both the foregoing general description and the following detailed description are exemplary and explanatory of preferred embodiments of the invention, and are not restrictive of the invention, as claimed.

DESCRIPTION OF PREFERRED EMBODIMENTS

Figure 1:
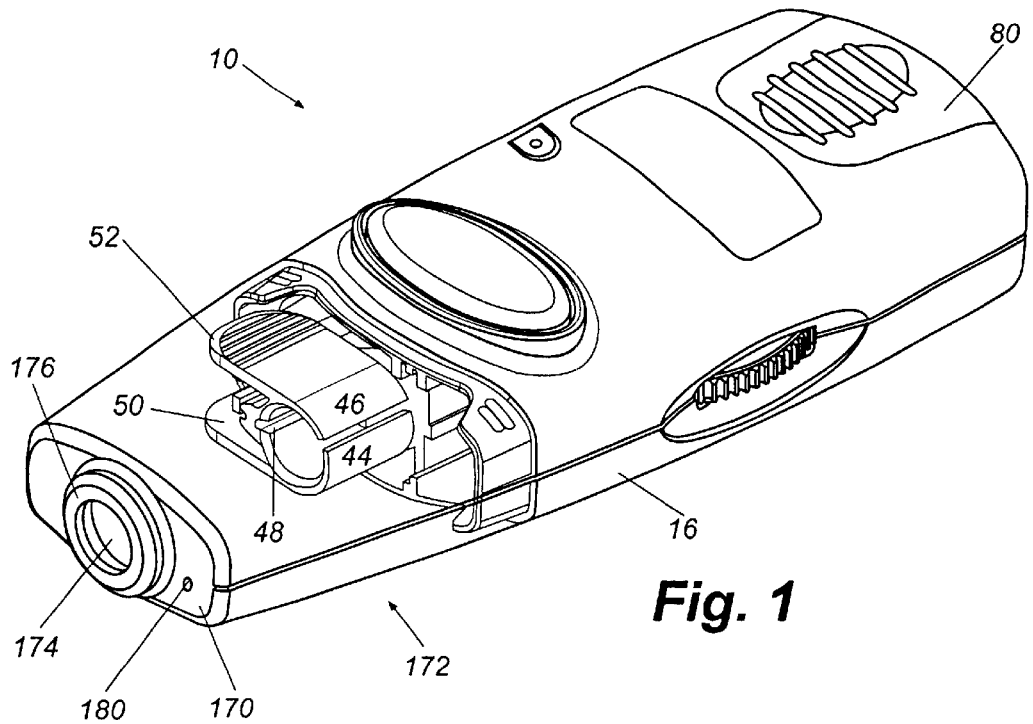
FIG. 1 is a perspective view of a lancing device according to a preferred embodiment of the present invention.

Example embodiments of the present invention are described herein with reference to the drawing figures. It will be understood that the described embodiments are by way of example only, and are not intended to be exhaustive or limiting of the scope of the claimed invention. It will also be understood that the various features and embodiments described have individual utility as well as utility in their various combinations thereof.

Figure 13:
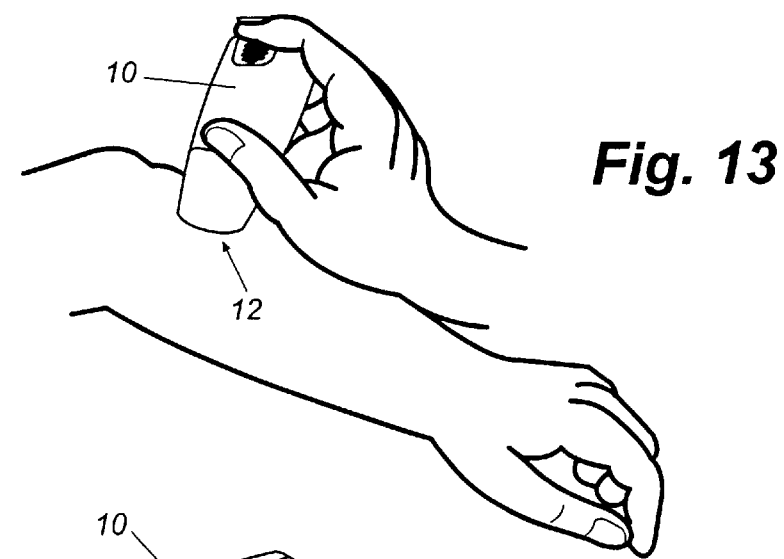
FIG. 13 shows a user lancing a forearm sampling site using a lancing device according to a preferred form of the present invention.
Figure 14:
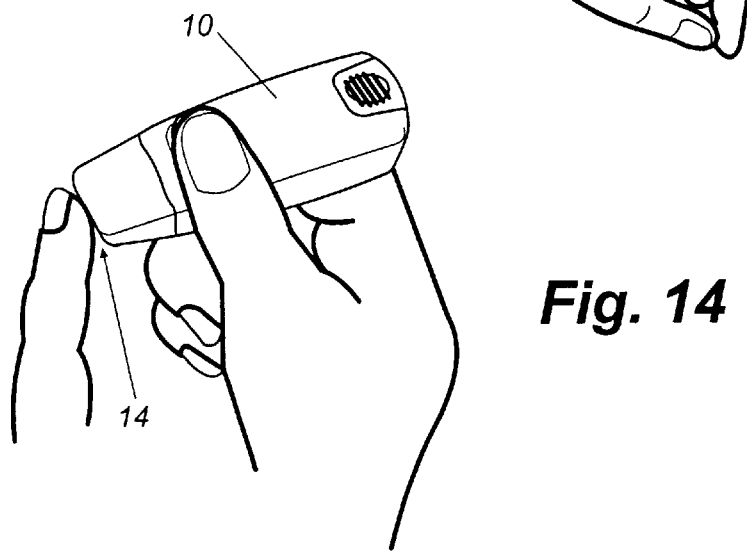
FIG. 14 shows a user lancing a fingertip sampling site using a lancing device according to a preferred form of the present invention.

According to a preferred embodiment, and with particular reference first to FIG. 1, the present invention comprises a lancing device 10 for penetrating body tissue of a human or animal subject to faciliate collection of a sample of a body fluid such as blood or interstitial fluid. As seen with reference to FIG. 13, the lancing device 10 is well suited for use in self-sampling from a forearm sampling site 12 of the subject or, as seen with reference to FIG. 14, from a fingertip sampling site 14 of the subject.

The lancing device 10 preferably comprises an exterior housing 16 having a housing geometry configured for ease of use, even by users suffering from impaired dexterity or eyesight. As described herein, the housing 16 includes the overall outer envelope of the lancing device 10 and, in an example embodiment described in greater detail below, comprises an endcap and front and back housing shells. The housing geometry preferably comprises a length L defined between a forward end 20 and a rear end 22, a width W defined between a first side 24 and a second side 26, and a thickness t defined between a front 28 and a back 30. In preferred form, the housing 16 is generally symmetric about perpendicular first and second central planes of symmetry 32, 34, and the stroke of a lancet carried by the lancing device 10 extends generally linearly along a central axis defined by the intersection of the first and second central planes of symmetry 32, 34. In preferred form, the overall length L is less than four times, and more preferably less than three times the overall width W This aspect ratio (i.e., L/W) of no more than 4:1, and more preferably no more than 3:1, provides the lancing device 10 with improved stability in use, which is of particular benefit in enabling users with impaired dexterity to apply pressure between the forward end 20 and a sampling site. According to preferred form, the overall width W of the lancing device 10 is at least 1½ times, and more preferably about twice the overall thickness t. This transverse ratio (W/t) of at least 3:2, and more preferably about 2:1, provides an easy to grip device which resists twisting about the central axis. As used herein, "overall" dimensions refer to dimensions of the main portion of the housing, not including any irregular portions such as sharp projections or recesses therefrom or therein. The rear end 22 preferably comprises a generally flat rear panel without edges or sharp radii, generally perpendicular to the stroke of a lancet carried by the lancing device 10, and preferably has a gradual radius of curvature to generally conform to the palm, finger or other portion of a human hand. The forward end 20 preferably also comprises a generally flat forward panel oriented generally perpendicular to the stroke of a lancet carried by the lancing device 10. The housing 16 is preferably generally rectangular, and its major exterior surfaces (e.g., the first and second sides, the front, the back, and the forward and rear ends) are generally perpendicular or parallel to the central axis. Edges at the intersections of major surfaces are preferably radiused to provide comfort in use. So configured, a user can easily apply pressure sufficient for sampling, between the forward end 20 and a sampling site, by applying compressive force to the rear end 22 in an axial direction, while maintaining the device in a stable and upright position, as shown for example in FIG. 13. In this manner, the stroke of the lancet is oriented generally perpendicular to the skin at the sampling site, to provide a straight in-straight out lancing of the skin for improved user comfort. According to a presently preferred form, the housing 16 has a maximum overall length of about 100 mm, and is preferably between about 40 mm to 100 mm, and more preferably between about 80 mm to 90 mm. The overall width is preferably at least about 25 mm, and more preferably between about 30 mm to 35 mm, at the widest portion of the housing. The overall thickness is preferably between about 10 mm to about 20 mm, and more preferably between about 15 mm to about 20 mm, at the thickest portion of the housing.

Figure 5:
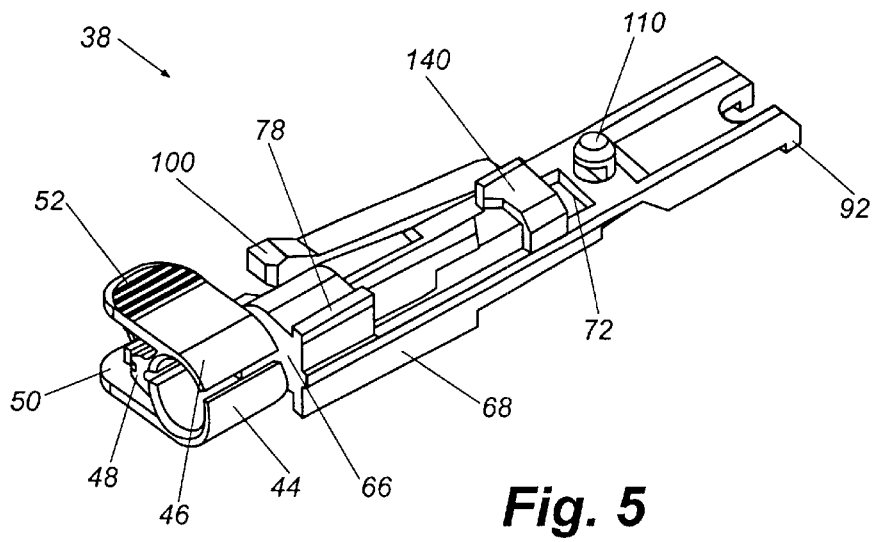
FIG. 5 is a detailed perspective view of a lancet carrier portion of the lancing device shown in FIG. 1.
Figure 4:
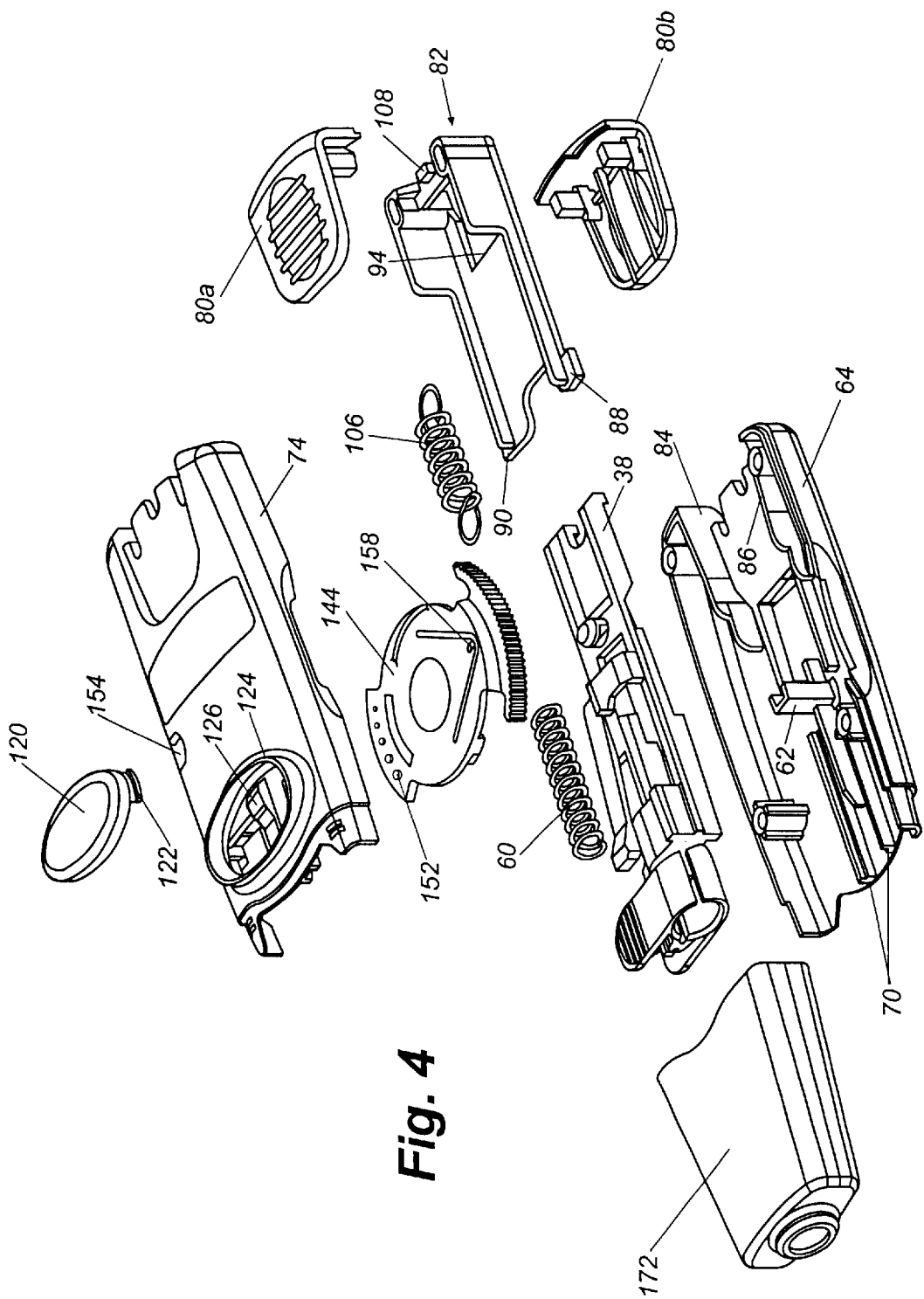
FIG. 4 is an exploded view of the lancing device shown in FIG. 1.
Figure 6:
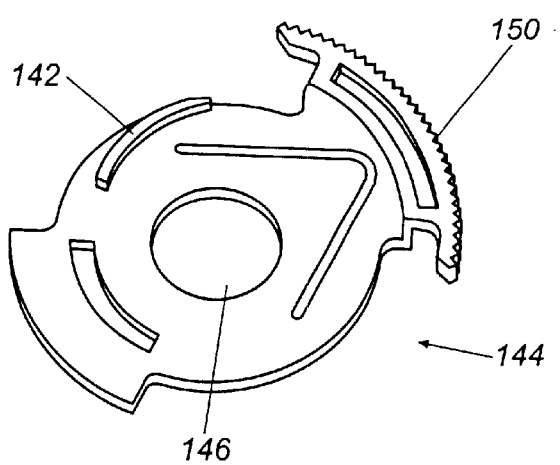
FIG. 6 is a perspective view of a stroke-control thumbwheel portion of the lancing device shown in FIG. 1.
Figure 9:
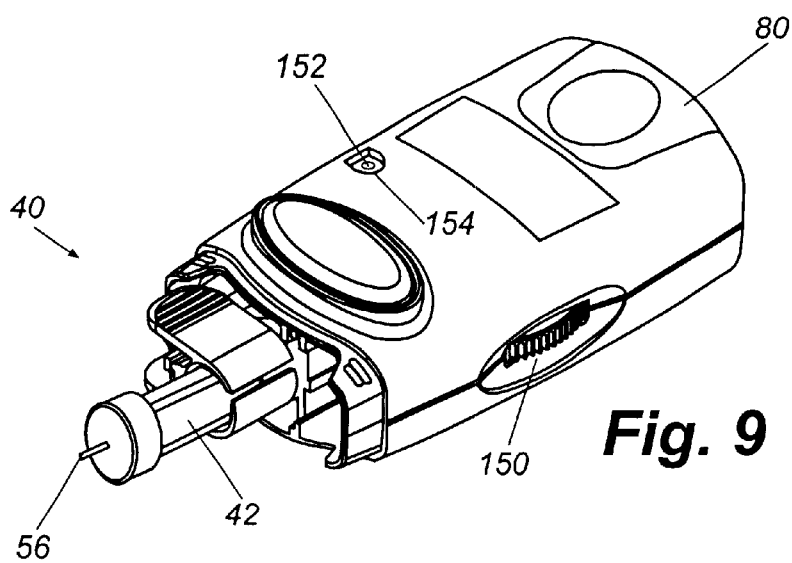
FIG. 9 is a perspective view of the lancing device shown in FIG. 1, with an endcap portion removed and a lancet installed.
Figure 10:
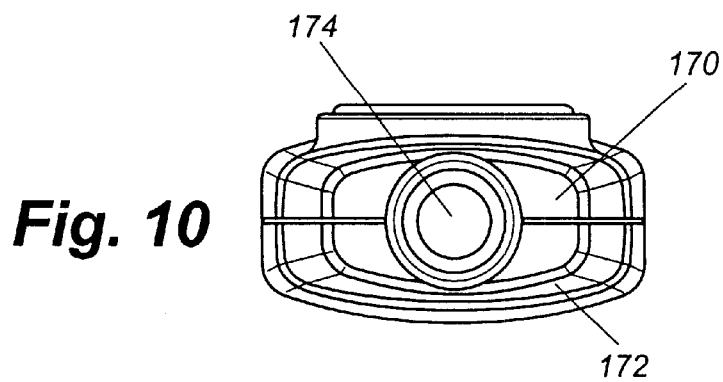
FIG. 10 is a forward end view of the lancing device shown in FIG. 1.
Figure 11:
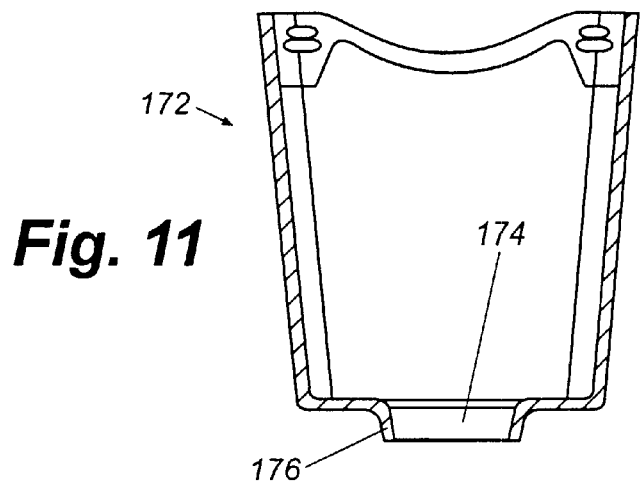
Figure 11 is a sectional view of an endcap portion of the lancing device shown in FIG. 1.

The lancing device 10 preferably further comprises a lancet carrier 38 comprising means 40 for releasably engaging a standard lancet 42, described with reference to FIGS. 4, 5 and 9. The lancing device 10 can be adapted for use with any of a number of commercially available lancets, and the lancets will typically have a needle diameter of between 30 gauge to 21 gauge, and more preferably about 25 gauge, although smaller or larger gauge needles may be suited for particular applications. The lancet carrier 38 is preferably formed from plastic, metal or other substantially rigid material(s), as by injection molding. In preferred form, the means 40 for releasably engaging a standard lancet 42 comprises a resilient clamp having a first gripping jaw 44 and a second gripping jaw 46 positioned in opposition to the first gripping jaw to define a lancet-receiving channel therebetween. The first and second gripping jaws 44, 46 are preferably movable between a closed position for gripping a lancet 42, and an open position for receiving and releasing the lancet 42 in a controlled manner. The means 40 for releasably engaging a standard lancet 42 preferably further comprises biasing means for biasing the first and second gripping jaws 44, 46 toward the closed position. According to a preferred embodiment depicted in the drawing figures, the first and second gripping jaws 44, 46 comprise opposed portions of an integrally formed split cylinder, and the biasing means comprises an intact portion of the cylinder, or an integrally formed spline 48 connecting the first and second gripping jaws 44, 46. Alternatively, the first and second gripping jaws 44, 46 can be separately formed, and the biasing means can comprise interacting portions of one or both jaws, and/or a separate biasing element such as a spring. In order to provide ease of insertion of a lancet 42 between the first and second gripping jaws 44, 46, and controlled release of the lancet therefrom, a first release arm 50 is provided, extending from the first gripping jaw 44, and a second release arm 52 is provided, extending from the second gripping jaw 46. The first and second release arms 50, 52 are preferably integrally formed with the first and second gripping jaws 44, 46, or alternatively can be separately formed and attached. Outer surface portions of the first and second release arms 50, 52 are preferably knurled, grooved, or otherwise textured to form a gripping surface. The first and second release arms 50, 52 preferably extend generally tangentially from the first and second gripping jaws 44, 46, opposite the free ends of the gripping jaws and beyond the biasing means, whereby application of force to the first and second release arms 50, 52 moves the first and second gripping jaws 44,46 toward their open position for easy and controlled insertion and release of a lancet 42. The knurled or grooved gripping surfaces allow a user to squeeze the first and second release arms 50, 52 together, as for example, between the user's thumb and forefinger, for insertion and removal of a lancet.

The lancet carrier 38 is preferably translationally mounted to slide within the housing 16 for carrying a lancet 42 along a reciprocating stroke from a retracted position wherein the lancet is substantially entirely within the housing, through a cocked position, to an extended position wherein at least a tissue-penetrating portion 56 of the lancet extends a distance outwardly beyond the housing, and back to the retracted position. The lancing device 10 preferably further comprises a cocking mechanism for shifting the lancet carrier from the retracted position to the cocked position, driving means for driving the lancet 42 from the cocked position to the extended position, and retraction means for returning the lancet carrier from the extended position to the retracted position. The driving means for driving the lancet 42 from the cocked position to the extended position preferably comprises a compression spring 60 engaged between a post 62 extending from a back housing shell 64 and a partition 66 of the lancet carrier 38. The compression spring 60 biases the lancet carrier 38 toward its extended position, and serves to propel the lancet carrier along a tissue-penetration portion of its stroke. The lancet carrier 38 preferably comprises one or more rails 68 adapted to slide in engagement with one or more fins 70 formed on the interior face of the back housing shell 64, and the post 62 extends through a slot 72 in the lancet carrier 38, thereby constraining the lancet carrier to slide generally linearly parallel to the central axis of the housing 16. The interior surface of a front housing shell 74 preferably comprises a channel 76 for engaging a cooperating rib 78 of the lancet carrier 38 to guide the lancet carrier 38 along a generally linear stroke. Upon assembly, the front and back housing shells 74, 64 are coupled, as by crush pins, fasteners, adhesive, or other attachment means, and the lancet carrier 38 is preferably constrained therebetween to a well-guided, generally linear stroke along or adjacent the central axis of the housing 16, whereby the lancet is driven along a straight in-straight out path, penetrating the skin of the sampling site at an angle generally perpendicular to the skin surface.

Figure 8:
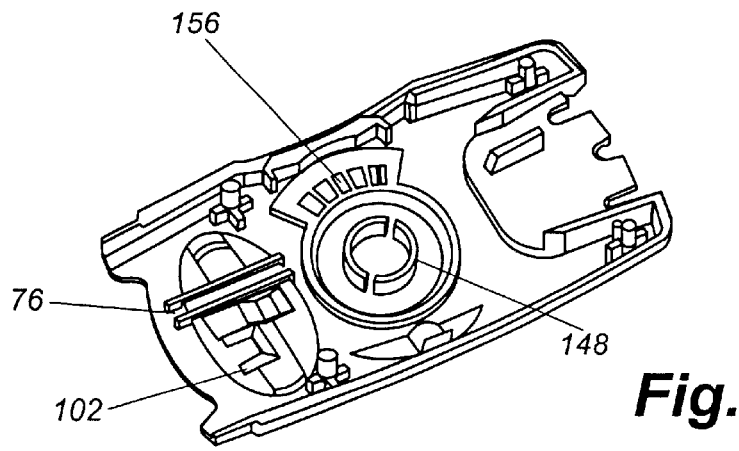
FIG. 8 is a perspective view showing the underside of a housing shell portion of the lancing device shown in FIG. 1.
Figure 12:
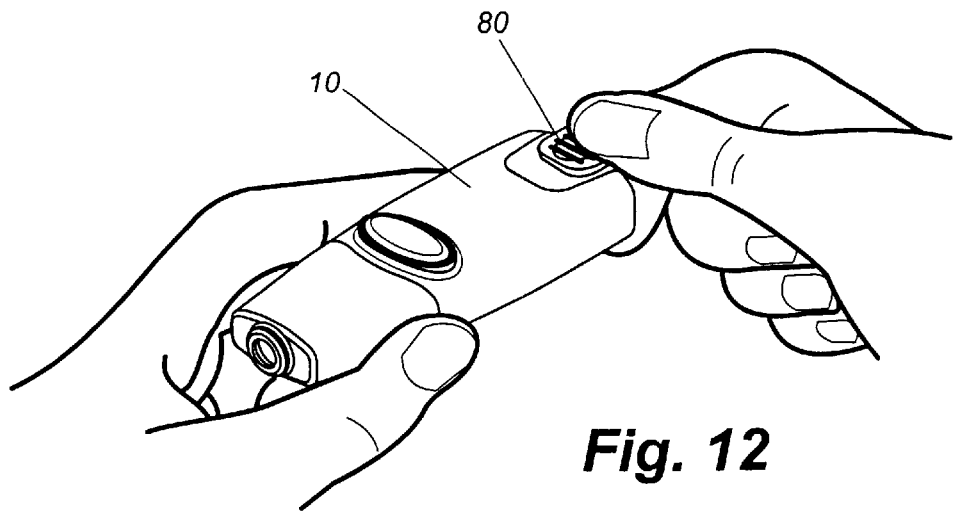
FIG. 12 shows a user cocking a lancing device according to a preferred form of the present invention.

The cocking mechanism arms the lancing device 10 by placing the spring 60 into compression, storing potential energy which is converted to kinetic energy as the lancet is driven through the tissue-penetrating portion of its stroke. The cocking mechanism is preferably actuated by the user by grasping a cocking actuator 80 adjacent the rear end 22 and pulling the cocking actuator away from the housing 16, as shown in FIG. 12. In a preferred embodiment, the cocking actuator comprises first and second halves 80a, 80b, that are attached to opposite sides of a cocking carriage 82 by pin connections. The cocking carriage 82 slides between opposed partitions 84, 86 of the back housing shell 64, and includes a pair of shoulders 88, 90 for abutting the ends of the partitions to limit the traverse of the cocking carriage 82. One or more lips 92 are preferably formed adjacent the rearward end of the lancet carrier 38, and project over an edge 94 of the cocking carriage 82, whereby retraction of the cocking carriage as shown in FIG. 12 draws the lancet carrier rearward into a cocked position in which the spring 60 is compressed. As the lancet carrier 38 is drawn into its cocked position, the tip of a cantilevered retaining finger 100 rides over an inclined ramp 102 formed on the interior surface of a front housing shell 74, as shown in FIG. 8. The retaining finger 100 flexes as it passes over the ramp 102, and snaps to rest on an upper surface of the ramp to retain the lancet carrier 38 in its cocked position until released by the triggering mechanism described below.

A return spring 106 is preferably coupled between a first retaining lug 108 on the cocking carriage 82 and a second retaining lug 110 on the lancet carrier 38, to draw the cocking actuator 80 back against the housing 16 after the lancing device is cocked. The return spring 106 also serves to retract the lancet carrier from its extended position to its retracted position after triggering the device, thereby withdrawing the tissue-penetrating portion 56 from the tissue of the sampling site to minimize any pain experienced by the subject. As will be understood by those skilled in the art, the compression spring 60 is relatively stiffer than the return spring 106 so that upon triggering the device, the compression spring drives the lancet carrier 38 through its entire stroke, from the cocked position to the extended position, before the return spring withdraws the lancet carrier. The return spring 106 is preferably an expansion spring, rather than a compression spring, whereby the return spring returns the lancet carrier to its retracted position without significant oscillation. By appropriately balancing the spring 60 and the return spring 106, a smooth and quick stroke of the lancet carrier is achieved, and oscillation of the lancet carrier is minimized to ensure that the user experiences only a single stick by the lancet.

The lancing device 10 preferably further comprises a triggering mechanism for releasing the lancet carrier 38 from its cocked position. A trigger button 120 is preferably mounted on the front 28 of the housing 16, and includes one or more retaining clips 122 and a triggering pin that extends through the front housing shell 74 adjacent the upper surface of the ramp 102. A large trigger button 120 is preferably provided for ease of use, and preferably extends across substantially the entire width of the front face of the housing 16. For example, in an embodiment of the device having a housing width of about 30 mm, a trigger button 120 about 20 mm wide is provided. The trigger button is preferably arranged generally centrally along the front 28 of the housing, approximately midway between the forward end 20 and the rear end 22, where a user can easily trigger the device while pressing the forward end of the device against a sampling site. For example, in an embodiment of the device having a housing length of about 87 mm, the trigger button 120 is located about 40 mm from the forward end 20. The size and orientation of the trigger button, in combination with the above-described transverse ratio of the housing, have been found to provide superior ergonimics and ease of use, as the trigger button is within easy reach of a users thumb or finger in a variety of gripping positions. The back 30 opposite the trigger button 120 preferably comprises a generally broad, flat panel, so that a user can easily and comfortably grip the device, as between a thumb and forefinger, to depress the trigger button 120 with his/her thumb. The front housing shell 74 preferably includes a trigger recess 124 for receiving the trigger button 120. A spring 126 is preferably provided to bias the trigger button 120 outwardly. When the device is cocked and the tip of the retaining finger 100 is engaged against the upper surface of the ramp 102 to hold the lancet carrier 38 in its cocked position, the tip of the retaining finger presses against the triggering pin. When the user presses the trigger button 120, the triggering pin disengages the retaining finger from the upper surface of the ramp, releasing the lancet carrier 38, which is then driven by the compression spring 60 through the tissue-penetrating portion of its stroke to the extended position, whereupon the return spring 106 then retracts the lancet carrier 38 to its retracted position.

Figure 2:
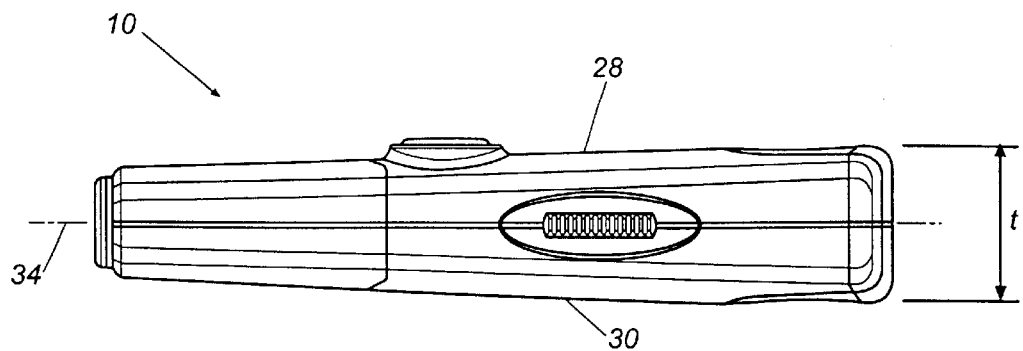
FIG. 2 is a side view of the lancing device shown in FIG. 1.
Figure 3:
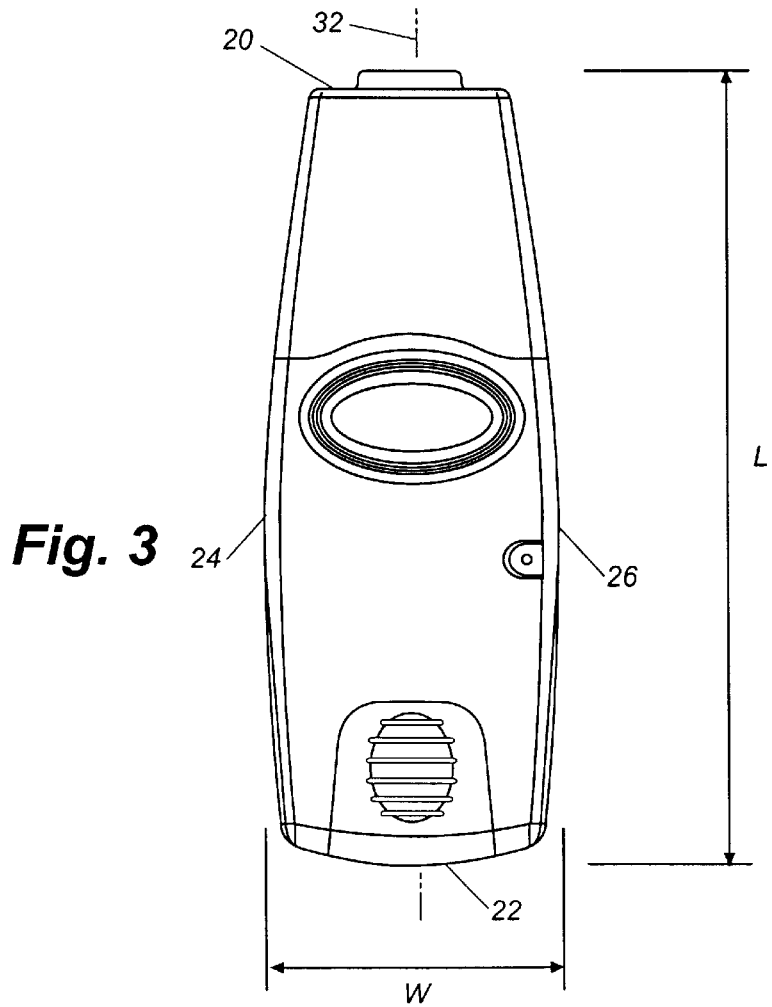
FIG. 3 is a front view of the lancing device shown in FIG. 1.
Figure 7:
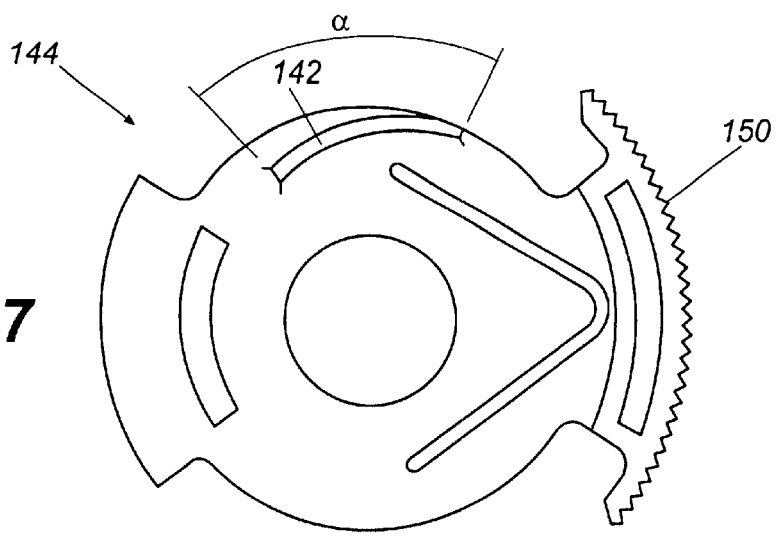
FIG. 7 is a plan view of the stroke-control thumbwheel portion shown in FIG. 6.

The lancing device 10 preferably further comprises stroke control means for controlling the stroke range, and thereby controlling the depth of penetration of the tissue penetration portion 56 of the lancet 42 into the body tissue of the sampling site. The stroke control means preferably comprises a limit member 140 attached to or comprises a portion of the lancet carrier 38, and a stop 142 attached to the housing 16. Contact between the limit member 140 and the stop 142 limits the range of the stroke of the lancet carrier 38 in the forward direction, and defines the extended position of the lancet carrier. In preferred form, the stroke control means is adjustable to permit the user to selectively adjust the stroke range and thereby varying the depth of penetration of the tissue penetration portion 56 of the lancet 42 into the body tissue of the sampling site. In preferred form, a selectively movable stop 142 permits the user to adjust the stroke range by varying the position at which the limit member 140 contacts the stop 142 to stop the forward travel of the lancet carrier 38. According to a preferred embodiment understood best with reference to FIGS. 2, 8 and 9, the stroke adjustment means comprises a thumbwheel 144 rotatably mounted to the housing 16. As used herein, the term "thumbwheel" includes rotating dials or other elements, translating slide mechanisms, or other movable stop mechanisms, that are manipulable in any way by the user, and specifically is not limited to elements manipulable by the thumb of a user or by any particular body part of the user. A central opening 146 in the thumbwheel 144 preferably receives a split-ring axle 148 on the front housing shell 74, whereby the axis of rotation of the thumbwheel is not aligned with, and more preferably is generally perpendicular to, the central axis of the housing. Alternatively, a solid ring axle can be provided. The thumbwheel 144 preferably carries the stop 142, and the stop 142 comprises an eccentric contact surface, whereby rotation of the thumbwheel varies the point of contact by the limit member 140, forward and rearward in the direction of the central axis of the housing, to limit the range of the stroke of the lancet carrier 38 in the forward direction. For example, as seen in FIG. 7, the stop 142 comprises an eccentric surface that spans an arc α of approximately 30° to 50° along the thumbwheel, and is eccentrically offset approximately 2 mm. In this manner, selective rotation of the thumbwheel 144 by the user through the span of the arc a varies the depth of penetration of the tissue penetration portion 56 of the lancet 42 from a depth of approximately 0.025 inch to approximately 0.100 inch. Alternatively, the thumbwheel can comprise an eccentric surface spanning an arc of less than 30° or more than 50°. By directly controlling the stroke range, the present invention reduces tolerance stacking and provides more consistent control of the penetration depth than some previously known devices that use interchangeable or screw-adjusted end caps for control of penetration depth. The thumbwheel 144 is preferably mounted generally midway along the length of the housing 16. A ribbed, knurled, or otherwise textured edge portion 150 of the thumbwheel 144 preferably projects from one or both of the first and second sides 24, 26, to facilitate depth adjustment. A portion of the side(s) of the housing 16 may be recessed to permit access to the thumbwheel for adjustment, while shielding the thumbwheel against inadvertent contact during use of the device.

The lancing device 10 preferably further comprises a depth indicator for indicating the set stroke range and, correspondingly, the depth of penetration of the tissue penetration portion 56 of the lancet 42 into the skin. According to a preferred embodiment, the depth indicator comprises indicia 152 on the thumbwheel 144, and a cooperating opening or window 154 through the housing for displaying the indicia. In still further preferred embodiments, the stroke adjustment means of the lancing device 10 further comprises indexing means for allowing the user to increment the forward extent of the stroke range, and accordingly the penetration depth, through a plurality of discrete positions. In preferred form, the indexing means comprises an arcuate series of detents 156 on the interior of the front housing shell 74, and one or more cooperating projections 158 formed on the thumbwheel 144. Rotation of the thumbwheel 144 causes the projection(s) 158 to ride over the series of detents 156, providing tactile feedback to the user.

The present invention preferably further comprises a lancing device 10 having a pressure applicator for tensioning skin at the sample site through the application of compressive pressure against the sample site, and for stimulating the generation of a sample of body fluid of a desired quantity. In preferred form, the pressure applicator portion of the lancing device is adjacent or surrounds the path of the tissue penetrating portion 56 as the lancet traverses its stroke toward the extended position. In this manner, the lancing device need not be repositioned for pressure application after the tissue is pierced. The pressure applicator preferably comprises a forward panel 170 adjacent or forming the forward end 20 of the housing 16. In preferred form, the forward panel 170 comprises the forward end of an end cap 172 that is releasably attached to the forward ends of the assembled front and back housing shells 74, 64. The endcap 172 is shown attached in FIG. 1, and detached in FIG. 9. The forward panel 170 preferably defines an opening 174 therethrough, for allowing passage of at least the tissue penetrating portion 56 of a lancet 42 towards its extended position. A raised lip 176 preferably projects a distance forward from the forward panel, and surrounds at least a portion of the opening 174. In preferred form, the opening 174 is between about 4 mm to 8 mm in diameter. More preferably, the opening 174 is less than about 6 mm in diameter, so that a standard lancet will not pass therethrough, thereby reducing the risk that the lancet will be released from containment within the end cap 172. An opening diameter of about 6 mm is presently considered to provide superior sample collection results, while preventing release of the lancet. The raised lip 176 preferably comprises an annular ring surrounding the opening 174, and projects forward from the forward panel 170 a distance of between about 1 mm to 3 mm, and most preferably about 2 mm. The annular ring preferably presents a generally forward-facing annular land about 2 mm across. The disclosed dimensions of the opening 174 and the raised lip 176 have been found to produce surprisingly superior results in stimulating sample generation without undue discomfort or bruising to the subject, and without leaving appreciable compression marks on the skin surrounding the sampling site, when used according to the sampling procedures herein described. In particular, it is believed that the provision of the generally flat forward panel 170 reduces discomfort to the user by distributing compressive pressure over a larger surface area at the sampling site and limiting the extent to which the raised lip 176 may compress the skin and underlying tissue at the sampling site. The provision of a raised lip 176 having the stated dimensions, and provided with the above-described annular land, further limits the depth of compression and reduces user discomfort that might result from compression with a sharper contact surface.

The present invention preferably further comprises a lancing device 10 having a transparent portion adjacent the forward end 20 to permit the subject to visually observe the size of a drop of blood or other fluid sample being collected. In a preferred embodiment, the entire end cap 172 is formed from a transparent material such as a clear plastic. Alternatively, the transparent portion comprises a wall or window of transparent material or a view hole or opening provided in an otherwise translucent or opaque portion of the end cap 172 or other portion of the housing 16. The transparent portion is positioned to permit observation of the sample site through the opening 174 after the tissue penetrating portion 56 has pierced the tissue of the sample site. The combination of the transparent portion with the adjacent pressure applicator described above advantageously permits the user to observe the sampling site and monitor the sample size as pressure is applied to stimulate sample generation. In a further preferred embodiment, sample size indicia 180 are provided adjacent the opening 174, most preferably on the interior surface of the forward panel 170, to provide a size reference for comparison with the size of the drop of blood or other fluid sample being collected. In an example embodiment, the sample size indicia 180 is a circular mark having a diameter equal to the diameter of a blood drop of the requisite fluid volume required for analysis using a standard blood glucose testing system.

The present invention further comprises a method of collecting a sample of a body fluid. The method of the present invention preferably comprises forming an opening in a body tissue such as skin at a sample site of the tissue, using a lancing device. In preferred form, the lancing device comprises a lancet having a tissue penetrating portion, a pressure applicator, and a transparent portion, substantially as described herein. For example, with reference to the above-described lancing device 10, the step of forming an opening in a body tissue can comprise: removing an end cap 172 from the lancing device; loading a lancet between the jaws 44,46 of a lancet carrier 38; replacing the end cap; adjusting the stroke control means to the desired depth of penetration; cocking the lancing device; pressing the forward panel 170 against the forearm, finger or other sampling site; and pressing the trigger button 120 to release the lancet carrier. The lancet is driven from its cocked position to its extended position, whereupon the tissue penetrating portion of the lancet forms an opening in the tissue at the sampling site, and then is retracted to its retracted position via the return spring 106. The opening 174 and raised lip 176 cooperate to tension the skin at the sampling site during and after the penetration of the tissue. Thus, it may be preferable to apply slight or moderate compressive pressure to the sampling site with the pressure applicator prior to the lancet stick, to pre-tension the skin at the sampling site and cause skin at the sampling site to bulge into the opening 174. Alternatively, the forward end of the device can be placed in light contact with the sampling site prior to the lancet stick, and increased pressure applied after the stick. The method of the present invention preferably further comprises applying compressive pressure after the puncture to the sampling site with a pressure applicator portion of the lancing device to stimulate the flow of a body fluid such as blood through the opening in the tissue at the sampling site. The opening 174 and raised lip 176 tension the tissue to open the wound and generate a flow of body fluid. Steady compressive pressure or varying compressive pressure, as by pumping the device against the sampling site, can be applied. As pressure is applied, the sample site is preferably observed through a transparent portion of the lancing device. If a sample size indicia is provided, the collected sample of body fluid is monitored in comparison to the sample size indicia. When the collected sample grows to the requisite size, the device is removed from the sample site. Removal of the pressure applied by the device allows the wound to close, facilitating faster clotting and healing, and reducing or eliminating the extent of any residual bleeding that could stain the users clothing. The collected sample of body fluid is then subjected to analysis according to any of a variety of analytic techniques.

While the invention has been disclosed in preferred forms, it will be apparent to those skilled in the art that many modifications, additions, and deletions may be made therein without departing from the spirit and scope of the invention as set forth in the following claims.

What is claimed is:

1. A lancing device for use with a lancet to penetrate tissue and facilitate collection of a sample of a body fluid, said lancing device comprising:
   (a) a housing;
   (b) a lancet carrier translationally mounted to said housing for carrying a lancet along a stroke traversing to an extended position wherein a tissue penetrating portion of the lancet extends a distance outwardly of said housing, said lancet carrier comprising a limit member; and
   (c) a thumb wheel rotationally mounted to said housing about an axis of rotation generally perpendicular to a central axis of said housing, and comprising an eccentric contact surface forming a selectively movable stop for contacting said limit member to limit the stroke of the lancet carrier in the direction of the extended position.

2. The lancing device of claim 1, further comprising indicia on said thumbwheel for indicating the distance the tissue penetrating portion of the lancet extends outwardly of said housing in said extended position.

3. The lancing device of claim 1, further comprising indexing means for incrementing rotation of said thumbwheel relative to said housing through a plurality of discrete positions.

4. The lancing device of claim 3, wherein said indexing means comprises an arcuate series of detents formed in said housing and at least one cooperating projection formed on said thumbwheel.

5. The lancing device of claim 1, further comprising a pressure applicator, said pressure applicator comprising a forward panel of said housing defining an opening therethrough, and a raised lip surrounding at least a portion of said opening.

6. The lancing device of claim 1, wherein said housing comprises a releasable endcap, and wherein at least a portion of said endcap is transparent.

7. A lancing device for use with a lancet to penetrate tissue and facilitate collection of a sample of a body fluid, said lancing device comprising:
   (a) a housing;
   (b) a lancet carrier translationally mounted to said housing for carrying a lancet along a stroke traversing an extended position wherein a tissue penetrating portion of the lancet extends a distance outwardly of said housing, said lancet carrier comprising a limit member; and
   (c) a thumb wheel rotationally mounted to said housing, and comprising an eccentric contact surface forming a selectively movable stop for contacting said limit member to limit the stroke of the lancet carrier in the direction of the extended position,
   wherein said lancet carrier comprises a first gripping jaw, a second gripping jaw positioned in opposition to said first gripping jaw, biasing means for biasing said first and second gripping jaws from an open position for receiving and releasing a lancet towards a closed position for gripping a lancet, a first release arm extending from said first gripping jaw, and a second release arm extending from said second gripping jaw.

8. A lancing device for use with a lancet to penetrate tissue and facilitate collection of a sample of a body fluid, said lancing device comprising:
   (a) a housing;
   (b) a lancet carrier translationally mounted to said housing for carrying a lancet along a stroke traversing an extended position wherein a tissue penetrating portion of the lancet extends a distance outwardly of said housing, said lancet carrier comprising a limit member, and
   (c) a thumb wheel rotationally mounted to said housing, and comprising an eccentric contact surface forming a selectively movable stop for contacting said limit member to limit the stroke of the lancet carrier in the direction of the extended position,
   wherein said housing is generally symmetric about perpendicular first and second planes of symmetry, has an aspect ratio of no more than 4:1, and has a transverse ratio of at least 3:2.

9. A lancing device for use with a lancet to penetrate tissue and facilitate collection of a sample of a body fluid, said lancing device comprising:
   (a) a housing;
   (b) a lancet carrier mounted to said housing for releasably engaging a lancet, said lancet carrier comprising:
      (i) a first gripping jaw;

(ii) a second gripping jaw positioned in opposition to said first gripping jaw to define a lancet-receiving channel between said first and second gripping jaws, said first and second gripping jaws being movable between a closed position for gripping a lancet and an open position for receiving and releasing a lancet;

(iii) biasing means for biasing said first and second gripping jaws toward said closed position; and (iv) a first release arm connected to said first gripping jaw and a second release arm connected to said second gripping jaw, whereby application of force to said first and second release arms moves said first and second gripping jaws toward said open position.

10. The lancing device of claim 9, wherein said first and second gripping jaws comprise opposed portions of an integrally-formed split cylinder joined about a common hinge point.

* * * * *